US012672875B2

(12) United States Patent
Yevzlin

(10) Patent No.: US 12,672,875 B2
(45) Date of Patent: Jul. 7, 2026

(54) END TO END ANASTOMOTIC CONNECTOR

(71) Applicant: PHRAXIS INC., Minneapolis, MN (US)

(72) Inventor: Alexander S. Yevzlin, Black Earth, WI (US)

(73) Assignee: PHRAXIS INC., Minneapolis, MN (US)

( * ) Notice: Subject to any disclaimer, the term of this patent is extended or adjusted under 35 U.S.C. 154(b) by 0 days.

(21) Appl. No.: 16/957,455

(22) PCT Filed: Feb. 7, 2019

(86) PCT No.: PCT/US2019/016970
    § 371 (c)(1),
    (2) Date: Jun. 24, 2020

(87) PCT Pub. No.: WO2019/157128
    PCT Pub. Date: Aug. 15, 2019

(65) Prior Publication Data
    US 2021/0068836 A1     Mar. 11, 2021

Related U.S. Application Data

(60) Provisional application No. 62/628,043, filed on Feb. 8, 2018.

(51) Int. Cl.
    *A61B 17/11* (2006.01)
    *A61B 17/00* (2006.01)
    (Continued)

(52) U.S. Cl.
    CPC ..... *A61B 17/11* (2013.01); *A61B 2017/00526* (2013.01); *A61B 2017/00831* (2013.01);
    (Continued)

(58) Field of Classification Search
    CPC .......... A61B 17/11; A61B 2017/00526; A61B 2017/00831; A61B 2017/00867;
    (Continued)

(56) References Cited

U.S. PATENT DOCUMENTS 3,818,511 A     6/1974   Goldberg et al.
4,352,358 A    10/1982   Angelchik
                (Continued)

FOREIGN PATENT DOCUMENTS

CA     2366703 A1     9/2000
CA     2574941 A1     7/2007
                (Continued)

OTHER PUBLICATIONS

Japanese Final Rejection Office Action, issued by the Japanese Patent Office regarding corresponding patent application Serial No. JP 2014-516024; mailed dated Jun. 4, 2015; 5 pages.
(Continued)

*Primary Examiner* — Jing Rui Ou
(74) *Attorney, Agent, or Firm* — Fox Rothschild LLP

(57) ABSTRACT

An end-to-end anastomotic connector is provided. The anastomotic connector includes solely an arterial connector and a venous connector. The inner diameter of the proximal end of the arterial connector is sized to directly receive the proximal end of the venous connector in an interference fit without the need for a graft material therebetween. The arterial connector and the venous connector are implanted in an artery and vein, respectively, to form a co-axial relationship with the respective vessel.

19 Claims, 6 Drawing Sheets

(51) Int. Cl.
    *A61F 2/852*         (2013.01)
    *A61F 2/915*         (2013.01)

(52) U.S. Cl.
    CPC .............. *A61B 2017/00867* (2013.01); *A61B*
          *2017/00938* (2013.01); *A61B 2017/1107*
        (2013.01); *A61B 2017/1132* (2013.01); *A61F*
        *2/852* (2013.01); *A61F 2/915* (2013.01)

(58) Field of Classification Search
    CPC .. A61B 2017/00938; A61B 2017/1107; A61B
                2017/1132; A61F 2/852
    See application file for complete search history.

(56)            References Cited

U.S. PATENT DOCUMENTS

| | | | |
|---|---|---|---|
| 4,368,736 A | 1/1983 | Kaster | |
| 4,512,761 A | 4/1985 | Raible | |
| 5,456,712 A | 10/1995 | Maginot | |
| 5,755,775 A | 5/1998 | Trerotola et al. | |
| 5,755,778 A | 5/1998 | Kleshinski | |
| 5,968,089 A | 10/1999 | Krajicek | |
| 5,972,017 A | 10/1999 | Berg et al. | |
| 6,030,392 A | 2/2000 | Dakov | |
| 6,030,395 A | 2/2000 | Nash et al. | |
| 6,035,856 A | 3/2000 | LaFontaine et al. | |
| 6,110,198 A * | 8/2000 | Fogarty ................... | A61F 2/915 |
| | | | 623/1.36 |
| 6,179,848 B1 | 1/2001 | Solem | |
| 6,190,590 B1 | 2/2001 | Randall et al. | |
| 6,210,429 B1 | 4/2001 | Vardi et al. | |
| 6,241,743 B1 | 6/2001 | Levin et al. | |
| 6,270,524 B1 | 8/2001 | Kim | |
| 6,277,133 B1 | 8/2001 | Kanesaka | |
| 6,293,955 B1 | 9/2001 | Houser et al. | |
| 6,402,767 B1 | 6/2002 | Nash et al. | |
| 6,419,681 B1 | 7/2002 | Vargas et al. | |
| 6,451,048 B1 | 9/2002 | Berg et al. | |
| 6,458,140 B2 | 10/2002 | Akin et al. | |
| 6,464,665 B1 | 10/2002 | Heuser | |
| 6,464,709 B2 | 10/2002 | Shennib et al. | |
| 6,482,214 B1 | 11/2002 | Sidor, Jr. et al. | |
| 6,485,513 B1 | 11/2002 | Fan | |
| 6,517,558 B2 | 2/2003 | Gittings et al. | |
| 6,582,463 B1 | 6/2003 | Mowry et al. | |
| 6,585,760 B1 | 7/2003 | Fogarty | |
| 6,599,303 B1 | 7/2003 | Peterson et al. | |
| 6,607,554 B2 | 8/2003 | Dang et al. | |
| D480,809 S | 10/2003 | Seibold et al. | |
| 6,648,901 B2 | 11/2003 | Fleischman et al. | |
| 6,682,540 B1 | 1/2004 | Sancoff et al. | |
| 6,719,781 B1 | 4/2004 | Kim | |
| 6,743,243 B1 | 6/2004 | Roy et al. | |
| 6,855,162 B2 | 2/2005 | Parodi | |
| 7,025,773 B2 | 4/2006 | Gittings et al. | |
| 7,056,326 B2 | 6/2006 | Bolduc et al. | |
| 7,105,020 B2 | 9/2006 | Greenberg et al. | |
| 7,175,652 B2 | 2/2007 | Cook et al. | |
| 7,267,680 B2 | 9/2007 | Wright | |
| 7,591,827 B2 | 9/2009 | Hill et al. | |
| 7,611,523 B2 | 11/2009 | Vargas et al. | |
| 7,691,140 B2 | 4/2010 | Bates et al. | |
| 7,722,665 B2 | 5/2010 | Anwar et al. | |
| 7,766,955 B2 | 8/2010 | Vardi et al. | |
| 7,828,834 B2 | 11/2010 | Garbe | |
| 7,850,725 B2 | 12/2010 | Vardi et al. | |
| 7,892,247 B2 | 2/2011 | Conston et al. | |
| 7,927,343 B2 | 4/2011 | Hill et al. | |
| 8,287,586 B2 | 10/2012 | Schaeffer et al. | |
| 8,298,251 B2 | 10/2012 | Golden et al. | |
| 8,343,204 B2 | 1/2013 | Osborne | |
| 8,361,092 B1 | 1/2013 | Asfora | |
| 8,366,651 B2 | 2/2013 | Dakin et al. | |
| 8,439,963 B2 | 5/2013 | Dickinson et al. | |
| 8,486,153 B2 | 7/2013 | Levine et al. | |

| | | | |
|---|---|---|---|
| 8,551,127 B2 | 10/2013 | Asfora et al. | |
| 8,628,583 B2 | 1/2014 | Meade et al. | |
| 8,715,336 B2 | 5/2014 | Chu et al. | |
| 8,728,145 B2 | 5/2014 | Chuter et al. | |
| 10,786,346 B2 | 9/2020 | Donadio, III et al. | |
| 2001/0044631 A1* | 11/2001 | Akin ...................... | A61F 2/064 |
| | | | 606/153 |
| 2001/0044649 A1 | 11/2001 | Vallana et al. | |
| 2001/0053929 A1* | 12/2001 | Vonesh ................... | A61F 2/07 |
| | | | 623/1.12 |
| 2002/0022853 A1 | 2/2002 | Swanson et al. | |
| 2002/0029079 A1* | 3/2002 | Kim ...................... | A61F 2/2493 |
| | | | 606/198 |
| 2002/0042647 A1 | 4/2002 | Jang | |
| 2002/0099392 A1 | 7/2002 | Mowry et al. | |
| 2002/0099393 A1 | 7/2002 | Fleischman et al. | |
| 2002/0123790 A1 | 9/2002 | White et al. | |
| 2003/0014102 A1 | 1/2003 | Hong et al. | |
| 2003/0070676 A1 | 4/2003 | Cooper et al. | |
| 2003/0109893 A1 | 6/2003 | Vargas et al. | |
| 2003/0125797 A1 | 7/2003 | Chobotov et al. | |
| 2003/0125799 A1 | 7/2003 | Limon | |
| 2003/0144578 A1 | 7/2003 | Koster | |
| 2003/0176878 A1 | 9/2003 | Bolduc et al. | |
| 2003/0216749 A1 | 11/2003 | Ishikawa et al. | |
| 2004/0097991 A1 | 5/2004 | Vargas et al. | |
| 2004/0102794 A1 | 5/2004 | Roy et al. | |
| 2004/0107004 A1 | 6/2004 | Levine et al. | |
| 2004/0116946 A1 | 6/2004 | Goldsteen et al. | |
| 2004/0133221 A1 | 7/2004 | Sancoff et al. | |
| 2005/0049675 A1 | 3/2005 | Wallace | |
| 2005/0049678 A1 | 3/2005 | Cocks et al. | |
| 2005/0137677 A1 | 6/2005 | Rush | |
| 2005/0154448 A1 | 7/2005 | Cully et al. | |
| 2005/0171598 A1 | 8/2005 | Schaeffer | |
| 2005/0182484 A1* | 8/2005 | Patel ...................... | A61F 2/06 |
| | | | 623/1.36 |
| 2005/0192604 A1 | 9/2005 | Carson et al. | |
| 2005/0228409 A1 | 10/2005 | Coppi | |
| 2005/0228484 A1* | 10/2005 | Stephens ................ | A61F 2/848 |
| | | | 623/1.21 |
| 2005/0267559 A1 | 12/2005 | De Oliveira | |
| 2005/0283173 A1 | 12/2005 | Abbott | |
| 2006/0004393 A1* | 1/2006 | Amarant ................ | A61B 17/11 |
| | | | 606/153 |
| 2006/0142840 A1 | 6/2006 | Sherry et al. | |
| 2007/0055358 A1 | 3/2007 | Krolik et al. | |
| 2007/0073388 A1 | 3/2007 | Krolik et al. | |
| 2007/0106313 A1 | 5/2007 | Golden et al. | |
| 2007/0179590 A1 | 8/2007 | Lu et al. | |
| 2007/0185567 A1 | 8/2007 | Heuser et al. | |
| 2007/0203572 A1 | 8/2007 | Heuser et al. | |
| 2007/0293940 A1 | 12/2007 | Schaeffer et al. | |
| 2008/0082159 A1 | 4/2008 | Tseng et al. | |
| 2008/0086190 A1 | 4/2008 | Ta | |
| 2008/0154290 A1 | 6/2008 | Golden et al. | |
| 2008/0161901 A1 | 7/2008 | Heuser et al. | |
| 2008/0288044 A1 | 11/2008 | Osborne | |
| 2009/0030502 A1 | 1/2009 | Sun et al. | |
| 2009/0036817 A1 | 2/2009 | Dakin et al. | |
| 2009/0076587 A1 | 3/2009 | Cully et al. | |
| 2009/0112237 A1 | 4/2009 | Paul, Jr. et al. | |
| 2009/0143793 A1 | 6/2009 | Chua et al. | |
| 2009/0209855 A1 | 8/2009 | Drilling et al. | |
| 2010/0003640 A1 | 1/2010 | Damstra et al. | |
| 2010/0010613 A1 | 1/2010 | Dorn | |
| 2010/0036401 A1 | 2/2010 | Navia | |
| 2010/0130995 A1 | 5/2010 | Yevzlin et al. | |
| 2010/0241218 A1 | 9/2010 | Bruszewski et al. | |
| 2010/0280612 A1 | 11/2010 | Helmus | |
| 2011/0031656 A1 | 2/2011 | Anneaux et al. | |
| 2011/0118821 A1 | 5/2011 | Brocker et al. | |
| 2011/0172684 A1 | 7/2011 | Granja Filho | |
| 2011/0184329 A1 | 7/2011 | Kramer et al. | |
| 2011/0208109 A1 | 8/2011 | Kassab | |
| 2011/0245851 A1 | 10/2011 | Ducharme et al. | |
| 2011/0264196 A1 | 10/2011 | Savage et al. | |
| 2011/0282368 A1 | 11/2011 | Swayze et al. | |

(56) References Cited

U.S. PATENT DOCUMENTS

| | | | |
|---|---|---|---|
| 2011/0306914 A1* | 12/2011 | Hartley .................... | A61F 2/07 |
| | | | 604/8 |
| 2012/0035708 A1 | 2/2012 | Paul, Jr. et al. | |
| 2012/0065652 A1 | 3/2012 | Cully et al. | |
| 2012/0123513 A1 | 5/2012 | Asfora et al. | |
| 2012/0290065 A1 | 11/2012 | Li et al. | |
| 2013/0018215 A1 | 1/2013 | Snider et al. | |
| 2013/0035752 A1 | 2/2013 | Chang | |
| 2013/0085565 A1 | 4/2013 | Eller et al. | |
| 2013/0274646 A1 | 10/2013 | Paris et al. | |
| 2014/0012065 A1 | 1/2014 | Fitzgerald et al. | |
| 2014/0018721 A1* | 1/2014 | Gage ................. | A61M 39/0247 |
| | | | 604/8 |
| 2014/0031785 A1 | 1/2014 | Schwagten et al. | |
| 2014/0088623 A1 | 3/2014 | Yevzlin et al. | |
| 2014/0088685 A1 | 3/2014 | Yevzlin et al. | |
| 2014/0121585 A1 | 5/2014 | Baker et al. | |
| 2014/0194910 A1 | 7/2014 | Orion et al. | |
| 2014/0294910 A1 | 10/2014 | Palmaz | |
| 2015/0134051 A1* | 5/2015 | Donadio ................. | A61F 2/848 |
| | | | 623/2.4 |
| 2015/0366580 A1 | 12/2015 | Lenihan et al. | |
| 2017/0000939 A1 | 1/2017 | Cully et al. | |
| 2017/0035423 A1 | 2/2017 | Shields et al. | |
| 2017/0196676 A1 | 7/2017 | Donadio et al. | |

FOREIGN PATENT DOCUMENTS

| | | | |
|---|---|---|---|
| CA | 2766347 A1 | 12/2010 | |
| CA | 2810671 A1 | 3/2012 | |
| JP | 2004516914 A | 6/2004 | |
| JP | 2006510393 A | 3/2006 | |
| JP | 2006523515 A | 10/2006 | |
| WO | WO-199802099 A1 | 1/1998 | |
| WO | WO-199819629 A2 | 5/1998 | |
| WO | WO-199819636 A2 | 5/1998 | |
| WO | WO-199945861 A1 | 9/1999 | |
| WO | WO-199962415 A1 | 12/1999 | |
| WO | 2000024339 A1 | 5/2000 | |
| WO | WO-200112074 A1 | 2/2001 | |
| WO | WO-200126562 A1 | 4/2001 | |
| WO | WO-2001026562 A1 | 4/2001 | |
| WO | WO-200149213 A2 | 7/2001 | |
| WO | WO-200258594 A1 | 8/2002 | |
| WO | WO-2002058594 A1 | 8/2002 | |
| WO | WO-2004010898 A1 | 2/2004 | |
| WO | WO-2004016201 A2 | 2/2004 | |
| WO | WO-2004093966 A1 | 11/2004 | |
| WO | WO-2006028925 A1 | 3/2006 | |
| WO | WO-2007024964 A1 | 3/2007 | |
| WO | WO-2008157283 A1 | 12/2008 | |
| WO | WO-20080157283 A1 | 12/2008 | |
| WO | WO-2009055651 A1 | 4/2009 | |
| WO | WO-2010121192 A1 | 10/2010 | |
| WO | 201114987 A2 | 12/2011 | |
| WO | WO-2012034108 A1 | 3/2012 | |
| WO | WO-2012117402 A1 | 9/2012 | |
| WO | 2013017639 A1 | 2/2013 | |
| WO | 2013187927 A1 | 12/2013 | |
| WO | 2015195668 A1 | 12/2015 | |
| WO | 2017040336 A1 | 3/2017 | |
| WO | 2017040366 A1 | 3/2017 | |

OTHER PUBLICATIONS

Japanese Final Rejection Office Action, issued by the Japanese Patent Office regarding corresponding patent application Serial No. JP 2014-514937; dated Jun. 10, 2015; 7pages.

Japanese Rejection Office Action, issued by the Japanese Patent Office regarding corresponding patent application Serial No. JP 2014-516037; dated Jun. 4, 2015; 8 pages.

International Search Report, issued by the United States Receiving Office, corresponding patent application Serial No. PCT/US2012/042666; mailed Sep. 13, 2012; 2 pages.

European Search Report issued by the European Patent Office, regarding correspondence patent application Serial No. 12799745.0; dated Feb. 12, 2015; 6 pages.

European Search Report issued by the European Patent Office, regarding correspondence patent application Serial No. 12800430.6; dated Feb. 17, 2015; 6 pages.

European Search Report issued by the European Patent Office regarding correspondence patent application Serial No. 12800335.7; dated Mar. 6, 2015; 6 pages.

International Search Report and Written Opinion issued by the ISA/U.S. Receiving Office, regarding corresponding application Serial No. PCT/US2012/042639; dated Sep. 25, 2012; 9 pages.

International Search Report and Written Opinion issued by the ISA/U.S. Receiving Office, regarding corresponding application Serial No. PCT/US2012/042688; dated Sep. 14, 2012; 9 pages.

International Search Report and Written Opinion issued by the ISA/U.S. Receiving Office, regarding corresponding application Serial No. PCT/US2012/067561; dated Apr. 22, 2013; 10 pages.

Japanese Rejection Office Action, issued by the Japanese Patent Office regarding corresponding patent application Serial No. 2015-517230; mailed Nov. 16, 2015; 8 pages (English translation).

Japanese Office Action issued by the Japanese Patent Office (translated), regarding corresponding patent application Serial No. 2014-516024, mailed Oct. 15, 2014; 5 pages.

Japanese Office Action issued by the Japanese Patent Office (translated), regarding corresponding patent application Serial No. 2014-514937, mailed Oct. 15, 2014; 6 pages.

Japanese Office Action issued by the Japanese Patent Office (translated), regarding corresponding patent application Serial No. 2014-516037, mailed Oct. 15, 2014; 5 pages.

European Communication pursuant to Article 94(3) EPC, issued by the European Patent Office, regarding corresponding patent application Serial No. EP 12799745.0, dated Dec. 20, 2016, 4 pages.

European Communication pursuant to Article 94(3) EPC, issued by the European Patent Office, regarding corresponding patent application Serial No. EP 12800430.6; dated Dec. 12, 2016, 4 pages.

"ANASTOMOSIS;" (n.d.) Dictionary.com Unabridged. Retrieved Jul. 30, 2017 from Dictionary.com website [http://www.dictionary.com/browse/anastomosis. 3 pages.

"TINE"; Merriam-Webster, n.d. Web. Aug. 22, 2018.

International Search Report and Written Opinion, issued by the ISA/U.S. Receiving Office, regarding related application Serial No. PCT/US2019/017200, dated May 6, 2019; 13 pages.

International Search Report and Written Opinion, issued by the ISA/U.S. Receiving Office, regarding related application Serial No. PCT/US2019/016970, dated May 8, 2019; 13 pages.

International Preliminary Report on Patentability issued by the International Bureau of WIPO, (Written Opinion dated Apr. 22, 2013), regarding corresponding application Serial No. PCT/US2012/067561; dated Dec. 24, 2014; 7 pages.

* cited by examiner

END TO END ANASTOMOTIC CONNECTOR

CROSS REFERENCE TO RELATED APPLICATIONS

This application is a U.S. national stage application of International Application Serial No.: PCT/US2019/016970, filed on Feb. 7, 2019, which claims priority to U.S. Provisional application Ser. No.: 62/628,043, filed on Feb. 8, 2018, the entireties of which are hereby incorporated by reference.

FIELD OF THE INVENTION

This invention relates to anastomotic connector devices. In particular, this invention relates to a vascular access device for use in hemodialysis and other procedures, such as in the cardiovascular field, where short-term and long-term access is required.

BACKGROUND OF THE INVENTION

In the United States alone, approximately 400,000 people have end-stage renal disease requiring chronic hemodialysis. Hemodialysis replaces kidney function by removing toxins from the blood that are normally removed by healthy kidneys In order to effectively remove toxins, blood must be passed at a high blood flow rate through a hemodialysis machine. This high blood flow is best achieved by the creation of a permanent vascular access site that includes an arteriovenous (AV) anastomosis in which a vein is attached to an artery to form a high-flow shunt or fistula.

Typically, a vein may be directly attached to an artery, but it takes from six to eight weeks before the fistula has sufficiently matured (time between placement and cannulation for dialysis) to provide adequate blood flow for use with hemodialysis. Moreover, a direct anastomosis may not be feasible in all patients due to anatomical considerations. Other patents may require the use of artificial graft material to provide an access site between the arterial and venous vascular systems. Because of the length of time required for a fistula to mature a patient needing dialysis will typically require a temporary access device, such as a Quinton catheter, to be inserted for hemodialysis access until the fistula has matured. The use of a temporary catheter access exposes the patient to additional risk of bleeding and infection, as well as discomfort, and is associated with a 91% higher mortality rate compared to fistulas. In trying to increase the prevalence of fistulas in the U.S., a proportional rise in catheter use has been documented.

Therefore, what is needed is an improved vascular access device that addresses the foregoing problems.

BRIEF SUMMARY OF THE INVENTION

The present invention addresses the foregoing problems by allowing a minimally invasive connection to be created between an artery and a vein in the arm of a patient without the need for creation of a surgical anastomosis.

In one aspect of the invention a device for connecting an artery and vein to create an arteriovenous anastomosis for hemodialysis is provided. The connector device includes a venous connector and an arterial connector. The arterial connector may comprise a stent constructed of a shape-memory material and optionally covered with a non-porous material to prevent leakage. The first (or distal) end of the arterial connector is sized to fit (~3-5 mm diameter) into a fluid arterial passageway of a patient and most preferably the radial artery of a patient and the second end (or proximal) is sized (~7 mm diameter) ta receive the second end (proximal) of the venous connector. In other words, the inner diameter of the proximal end of the arterial connector is greater than the outer diameter of the proximal end of the venous connector. Depending on the anatomy of a particular patient the length of the arterial and venous connectors may be from approximately 4 cm to 8 cm.

On another aspect of the invention, the venous connector may comprise a stent constructed of a shape-memory material and optionally covered with a non-porous material to prevent leakage. A first end (or distal) of the venous connector is sized (5-7 mm diameter) to fit into a fluid venous passageway of a patient and most preferably the cephalic vein of a patient. A second (proximal) end is configured to be received by the proximal end of the arterial connector. In other words, the proximal end of the venous connector has an outer diameter that is smaller than the inner diameter of the proximal end of the arterial connector. The first (distal) ends of the arterial and venous connectors may have an outer diameter that is greater than the outer diameter of the second (proximal) ends. Depending on the anatomy of a particular patient the length of the venous connector may be from approximately 4 cm to 8 cm.

Both the arterial connector and the venous connector may include an optional anchoring device at the first end thereof and in the case of the arterial connector optionally also at the second end thereof. The anchoring device may include one or more barbs on the first end, which extend radially outward from a longitudinal axis of the main body and are configured to secure the arterial or venous connector within the fluid passageway either by applying radial pressure to the vessel wall or by piercing anchoring the connector to the wall. In the case of a plurality of barbs comprising the anchoring device, the barbs may circumferentially surround the first end of the arterial or venous connector.

In another aspect of the invention, the two connectors are delivered into the radial artery and cephalic vein through a 3 cm incision via the Seldinger technique over a guide wire/sheath system individually. The two connectors may be inserted into one another to create a radial pressure/interference fit and a stay suture maybe placed at the site of pyre overlap between the two connectors.

In another aspect of the invention, the anastomotic connector couples the radial artery to the cephalic vein in the location of the forearm without the need for graft material connecting the two connectors.

In another aspect of the invention, a minimally invasive way to create a fistula using two connectors is provided. No graft material is required to join the two connectors.

In another aspect of the invention, the arterial connector is not a conventional "end to side" anastomotic connector but rather an "end to end" connector. An end-to-side anastomosis is one in which the arterial connector couples to the artery at a right angle or perpendicular to the arterial wall so as not to obstruct flow in the vessel. An end-to-end anastomosis is one in which the venous connector attaches to the vein in a way that the venous connector and vessel are coaxial.

In the present invention, the arterial and venous connectors as end-to-end because they accomplish a coaxial configuration with the vessel despite the entrance point.

BRIEF DESCRIPTION OF THE DRAWINGS

For a better understanding of the invention, and to show how the same may be carried into effect, reference will now be made, by way of example, to the accompanying drawings, in which.

DETAILED DESCRIPTION OF THE INVENTION

Figures 1A, 1B:
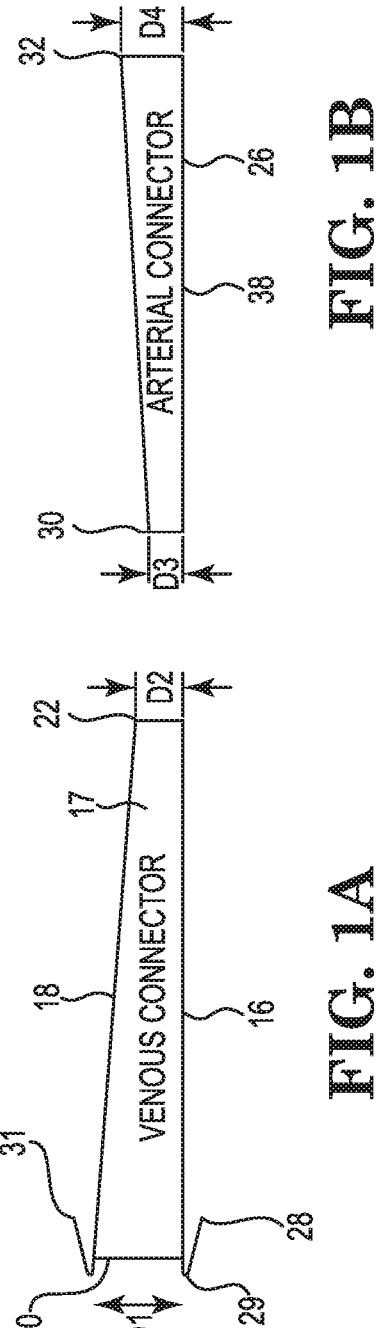
FIG. 1A is an illustration of the venous connector in accordance with the end to end arterial venous connector system in accordance with the invention.
FIG. 1B is an illustration of the arterial connector in accordance with the end to end arterial venous connector system in accordance with the invention.

Referring now to FIG. 1, an end-to-end anastomotic connector 10 is depicted. The anastomotic connecter 10 comprises a two-piece anastomotic connector that connects the radial artery 12 to the cephalic vein 14 in the location of the forearm without the need for graft material joining the two connectors together.

Figure 4:
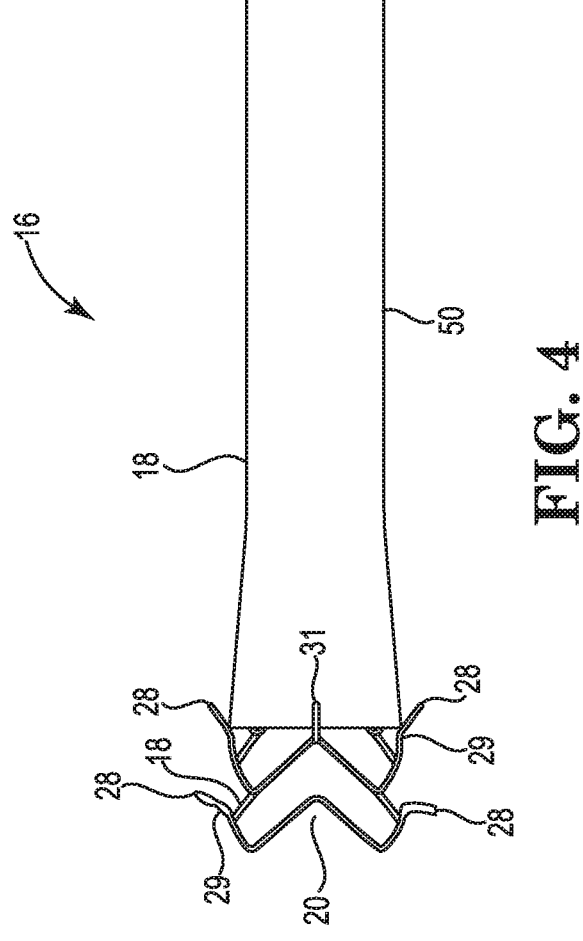
FIG. 4 is a view of the venous connector and/or arterial connector showing the optional biocompatible coating with the non-coated distal end.
Figure 5:
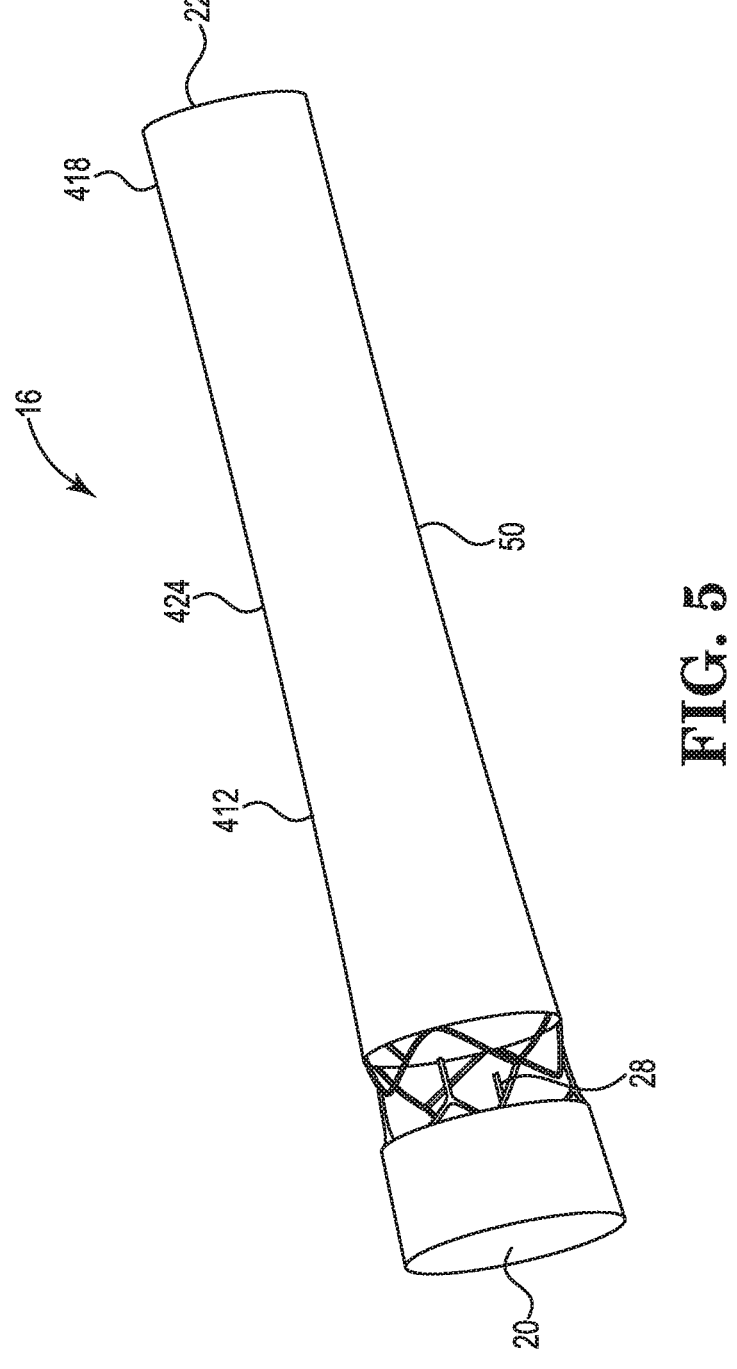
FIG. 5 is a view of the venous connector and/or arterial connector and showing a second aspect of the optional biocompatible coating showing a distal-most coated end with an optional non-coated anchoring device.

The venous connector 16 includes a conical-shaped body portion 18 having a first venous end 20 and a second venous end 22 and defines a lumen 17 having a blood flow path therethrough. The first venous end 20 may include an anchoring structure 28. Anchoring structure 28 may comprise a plurality of hooks, barbs, tines, prongs and other types of curved or angled fasteners designed to anchor the venous connector to an inner surface 40 of the venous wall 42. The anchoring structure 28 may circumferentially surround the first venous end 20. As seen in FIG. 4 the anchoring structure 28 may comprise a single row of barbs 28 that extend radially outward from a longitudinal axis of the venous connector to securely seat the connector against the venous wall 40 or may comprise two or more rows of barbs 28 as best seen in FIG. 5. A diameter D1 of the first venous end 20 is larger than a diameter D2 of the second end 22.

Figure 2:
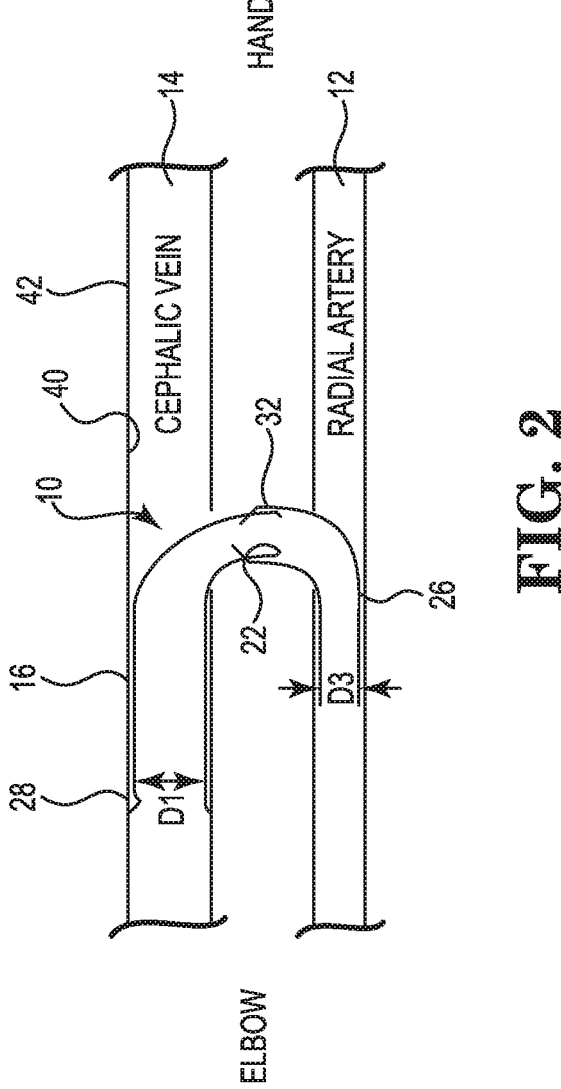
FIG. 2 is an illustration of the arterial connector coupled to the venous connector and inserted into an artery and vein, respectively.
Figure 3:
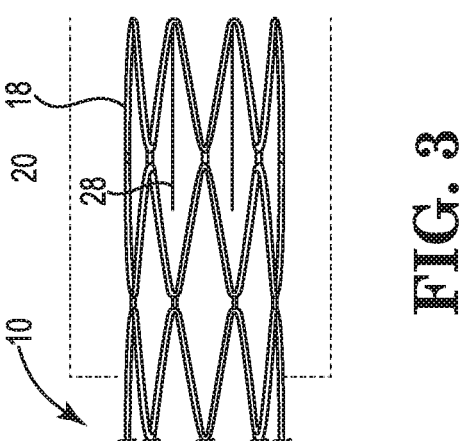
FIG. 3 is a detailed view of the body of the venous connector and/or arterial connector in accordance with the invention showing the optional anchoring device.

Conical-shaped body portion 18 may comprise a metal frame structure as best seen in FIG. 3. Those of skill in the art will appreciate, however, that the metal frame structure of the venous connector may include almost any configuration of struts and connectors known to those of skill in the art. The outer diameter of D1 of first end 20 of main body 18 is greater than the outer diameter D2 of second end 22 to ensure it is property seated in a venous fluid passageway. In addition, the outer diameter D2 is sized to ensure an interference fit within the second end 32 of arterial connector 26 as best seen in FIG. 2.

In one aspect of the venous connector depicted in FIG. 4 the first end 20, which is received within a vessel wall is non-coated or bare while the body 18 is coaled. Alternatively, some portions of the venous anchor may be coated while other portions may be non-coated to expose the anchoring structure 28 that circumferentially surrounds the first end as seen in FIG. 5. As will be appreciated by those of ordinary skill in the art, the venous anchor device 16 in accordance with the invention, and as best seen in FIGS. 4 end 5, is structured to provide a secure, leak-free connection to a venous vessel passageway. Therefore, it is contemplated that a fluid impermeable, biocompatible polymer 50 may be deposited on portions of the venous connector 16 to fill the interstices of the struts comprising the conical-shaped main body 18 to ensure a leak-tight seal when implanted in the venous fluid passageway. Such biocompatible materials may include, but are not limited to, expanded Polytetrafluoroethylene ("ePTFE"), polyester, silicone composites, or various other plastics and elastomers or combinations thereof. In an exemplary embodiment, the venous anchor device is coated with a PTFE. coating to prevent leakage of blood or other fluids from Lie portion of the device that transports fluid from the first anchor device through the graft and to the second anchor device. The PTFE coating is applied by a process including forming a dispersion of polymeric nanofibers, a fiberizing polymer, and a solvent, the dispersion having a viscosity of at least about 50,000 cPs. The venous connector 16 may be positioned over a tubular polymeric structure. Nanofibers from the dispersion are electrospun onto the tubular frame of the device and then the devices are heated. Alternatively, the venous anchor device is coated by extruding tubes of polytetrafluoroethylene (PTFE) on the inside of the device and one on the outside. The two layers that are formed are heated to meld together. Other polymers that may be useful in coating the present devices are fluorinatedethylenepropylene (FEP), perfluoroalkoxy (PFA), polyvinylidene fluoride (PVDF), tetrafluoroethylene, hexafluoropropylene, polyethylenes such as HDPE, MDPE and LDPE, polyethylene terepthalate polyester (PET), polyetheretherketone (PEEK) and similar polymers having low coefficients of friction.

As described previously and as alternatively depicted in FIG. 4 the first end 20 of the venous anchor device 16 may be left uncoated while the main body 18 is coated. Alternatively, as shown in FIG. 5, the venous connector 16 may have the distal-most portion of the first end 20 coated while the plurality of barbs 28 is uncoated to ensure barbs 18 are free to lie against vessel wall. Those of skill in the art will appreciate that barbs 18 may pierce the vessel wall or may simply lie adjacent the vessel wall without piercing it. The plurality of barbs 28 are configured to scat the venous connector in the vessel wall to ensure it docs not dislodge from the vessel wall. In addition, upon deployment barbs 28 restrict further expansion of the venous anchor device when the barbs 28 anchor it against the vessel wall. Those of skill in the art will appreciate that the distal end 29 of the barbs 28 is integrally formed with the metal frame structure of the main body 18 while the proximal end 31 is free or unattached like the tines of a comb or a pitchfork.

Those of skill in the art will appreciate that although it is contemplated that the venous connector 16 is coated there is no backflow in the venous connector due to the arterial pressure of the blood flowing through it. This minimizes any leakage that may occur at the entry point of the device in the venous wall. In addition, due to the arterial pressure those of skill in the art will appreciate that the proximal end of the venous connector would necessarily need to be inserted into the proximal end of the arterial connector.

Venous connector 16 may be cither self-expanding, such as so-called shape-memory materials, or non-self-expanding. such as stainless steel. In forming the exemplary venous connector, a tubular length of metal is used to cut the venous anchor device 16 and integrally form the struts and connectors of the main body 18 as well as barbs 28. As discussed previously, the metal material used in the exemplary venous connector 16 should be both resilient and capable of being heat treated to substantially set a desired shape. Preferably, the metal from which venous connector 16 is cut exhibits a high modulus of elasticity that is biocompatible and has superior compressibility allowing the venous connector 16 to be self-expandable.

One class of materials which meet these qualifications is so-called shape memory alloys. Such alloys tend to have a temperature induced phase change which will cause the material to have a preferred configuration which can be fixed by heating the material above a certain transition temperature to induce a change in the phase of the material. When the alloy is cooled back down, the alloy will "remember" rite shape it was in during the heat treatment and will tend to assume that configuration unless constrained from so doing.

One particularly preferred shape memory alloy for use in the present method is Nitinol, an approximately stoichiometric alloy of nickel and titanium, which may also include other minor amounts of other metals to achieve desired properties. NiTi alloys such as nitinol, including appropriate compositions and handling requirements, are well known in the art and such alloys need not be discussed in detail here.

Such NiTi alloys are preferred, at least in part, because they are commercially available, have a high yield strain and more is known about handling such alloys than other known shape memory alloys. NiTi alloys are also very elastic—they are said to be "superelastic" or "pseudoelastic." This elasticity will help a device of the invention return to a present expanded configuration for deployment into a blood vessel. However, any suitable self-expanding material may be used as will be appreciated by those of ordinary skill in the art.

As hereinafter described, prior to implantation the venous connector 16 is collapsed inside a delivery device or sheath. Upon introduction into a vessel, the first end 20 of the connector freely self-expands to its original dimensions. The self-expanding behavior of the venous connector 16 is due to the relatively high modulus of elasticity of the shape-memory material, which imparts superior spring-like properties to the venous connector 16.

The arterial connector 26 includes a substantially conically-shaped, resilient body portion 28 having a first (distal) arterial end 30 and a second (proximal) arterial end 32 and defines a lumen comprising a blood flow path therethrough. A diameter D3 of the first arterial end 30 is smaller than a diameter D4 of the second arterial end 32. The first end 30 is sized and configured to be positioned within a radial artery. The diameter D4 of the second arterial end 32 is larger than a diameter D2 of the second venous end 22. Thus, the second venous end 22 of venous connector 16 is configured to be received by the second arterial end 32 of the arterial connector 26 in an interference fit.

The arterial connector 26 may optionally include a plurality of finger-like tines 33 at the second or proximal end thereof as best seen in FIG. 2. Finger-like tines 33 extend inwardly from the main body 38 at an acute angle. However, those of skill in the art will appreciate that finger-like tines 33 can extend inwardly from the arterial connector 26 at any angle that will cause them to exert a compressive grasping force on the body of the venous connector 16 when operably coupled therewith. Because finger-like tines 33 extend outwardly from the arterial connector 26 they exert a compressive force on the venous connector 16 that prevents it from de-coupling from the arterial connector after placement. Those of skill in the art will also appreciate that the force of the arterial blood flow will also act to maintain the arterial connector 26 coupled to the venous connector 16.

It is contemplated that the man bodies 18, 38 of the venous connector 16 and the arterial connector will structurally be the same except for the presence of an anchoring device 28, which is optional on the arterial connector. If present, the anchoring device would be positioned circumferentially around the first arterial end 30. The main body portions of both the venous connector and arterial connector may comprise a single layer of shape-memory material or a two-layer construct without departing from the scope of the invention.

The frame-like structure of the arterial and venous connector has a loose configuration or in other words a column pitch (CP) that is substantially equivalent along the length of the device. In one aspect of the invention, the column pitch is approximately 0.185 inches which allows the connectors to easily bend. Those of skill in the art will appreciate, however, that other column pitches and other frame-like structures can be used and still be within the scope of the invention. When the venous connector is exposed to arterial pressure the loosely configured connector will stretch. When the two connectors are positioned within their respective vessels they will assume an outer diameter equal to the inner diameter of the vessel into which it is deployed. If optional anchoring devices are used, as they engage the vessel wall the anchoring device will prevent the vessel from further expansion.

Figure 6:
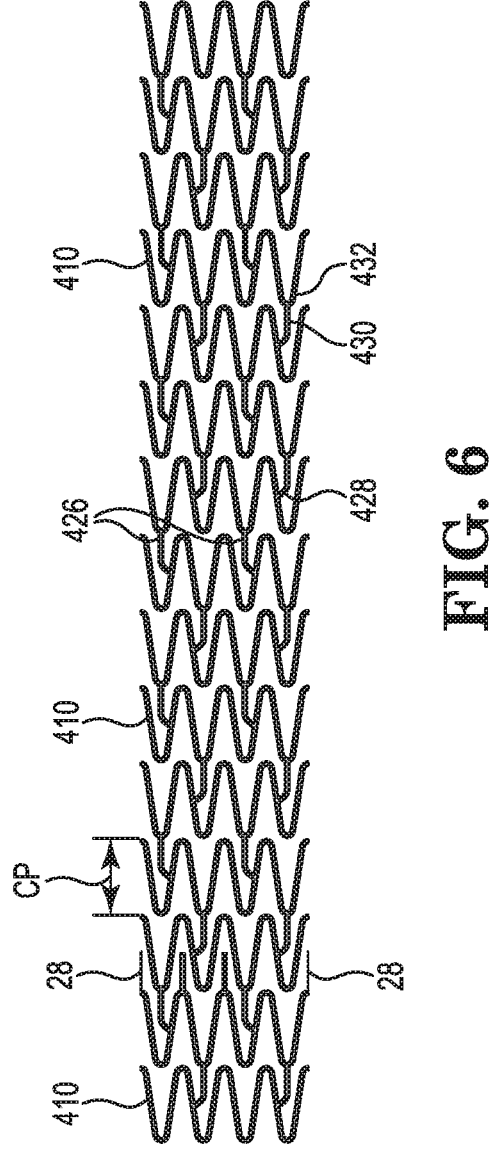
FIG. 6 is a view of the frame-work structure of he arterial and venous anchoring device laid flat in accordance with an aspect of the invention.

As can be seen in FIG. 6 the frame-like structure of the arterial and venous connector includes a plurality of rows 410 of openly-formed sinusoidal-shaped struts. Each row of sinusoidal-shaped struts 410 is connected to the subsequent row by two connecting members 426 that extend from a mid-portion of the strut to the curved portion of the strut in the subsequent row. Each row is connected to an adjacent row by two connecting members 426 each of said connecting members having a first portion 428 that extends radially from a mid-portion of the strut and a second portion 430 that extends axially from the first portion, the second portion 430 of the connecting member is connected to a peak 432 of the sinusoidal-shaped strut in the adjacent row.

Additionally, it may be preferable to provide the arterial 26 and venous 16 connectors of the invention with an inner surface that is contoured to allow smooth arterial or venous blood flow into and out of the connector devices. As those of ordinary skill in the art will appreciate, providing a non-thrombogenic surface minimizes the creation of recirculation or stagnation zones with high shear or dwell times that could otherwise lead to clotting.

It is also contemplated that the inner or outer surface of the arterial 26 and venous 16 connectors be configured to deliver and release therapeutic substances such as anti-microbial agents, anti-inflammatory agents, anti-proliferative agents (e.g. taclipaxel), growth factors, stem cells, collagen and the like. Those of ordinary skill in the art will appreciate that these therapeutic agents may be coupled with the connector and/or the external or internal surface of the connector by means such as being encased or embedded in the optional biocompatible coating, applied to a textured external surface of the connector; contained within pockets of the connector on either an internal or external surface, and the like.

The present invention provides a minimally invasive way to create an end-to-end fistula using two connectors without the need for graft material to couple the two connectors. The arterial connector comprises an end-to-end connector as opposed to the more conventional end-to-side connectors.

Based upon the present disclosure and after viewing the exemplary embodiment of the arterial and venous connectors 26, 16 presented herein, the many advantages and benefits provided by the invention will be appreciated by those of ordinary skill in tire art. One advantage is that the present invention provides a minimally invasive way to create an end-to-end fistula using two connectors without the need for graft material to couple the two connectors.

The arterial connector comprises an end-to-end connector as opposed to the conventional end-to-side connectors.

Another advantage is that the arterial and venous connectors of the invention may be implanted with minimally invasive surgery rather than with an "open surgery" approach. The implantation method is therefore less invasive for the patient and faster for the surgeon.

Although the present invention has been described with reference to preferred embodiments, workers skilled in the art will recognize that changes may be made in form and detail without departing from the spirit and scope of the invention.

What is claimed:

1. An anastomotic connector comprising:
an arterial connector having a distal arterial end co-axially implantable into an arterial passageway and a proximal arterial end, wherein an outer diameter of said distal arterial end is smaller than an outer diameter of said proximal arterial end; and
a venous connector having a distal venous end co-axially implantable into a venous passageway and a proximal venous end, wherein an outer diameter of the distal venous end is larger than an outer diameter of the proximal venous end, said venous connector having a substantially conical body comprising a frame structure including a plurality of struts and a plurality of interstices located between said struts and a fluid impermeable material deposited on said struts such that said fluid impermeable material fills the interstices;
wherein the inner diameter of the proximal arterial end is sized to receive the proximal venous end in an interference fit connection to form an anastomotic connector, the interference fit connection configured to be positioned at least partially outside the arterial passageway and the venous passageway, wherein the proximal venous end within the interference fit connection is bendable and configured to bend the anastomotic connector in an approximately U-shape when the arterial connector is deployed within the arterial passageway and the venous connector is deployed within the venous passageway;
wherein said venous connector includes an anchoring device that extends radially outwardly at an acute angle from a longitudinal axis of a tubular main body of the venous connector at the distal venous end; and
wherein said tubular main body of said venous connector is configured to stretch upon being exposed to arterial pressure while said anchoring device is configured to prevent expansion of the venous passageway.

2. The anastomotic connector of claim 1 wherein said anchoring device is configured to lie adjacent a venous vessel wall.

3. The anastomotic connector of claim 1 wherein said anchoring device is configured to penetrate a venous vessel wall to seat said anastomotic connector in a venous passageway.

4. The anastomotic connector of claim 1 wherein said arterial connector is coated with a fluid impermeable material.

5. The anastomotic connector of claim 4 wherein said fluid impermeable material is woven.

6. The anastomotic connector of claim 4 wherein said fluid impermeable material is a polymeric material.

7. The anastomotic connector of claim 4 wherein said fluid impermeable material is deposited onto said anastomotic connector by electrospinning.

8. The anastomotic connector of claim 4 wherein said fluid impermeable material is deposited onto said anastomotic connector by extrusion.

9. The anastomotic connector of claim 4 wherein said coating covers the entirety of said venous connector and said arterial connector.

10. The anastomotic connector of claim 4 wherein said coating covers the proximal end, a mid-portion and the distal end of said venous connector such that an anchoring device at the distal venous end remains uncoated.

11. The anastomotic connector of claim 1 wherein said venous connector and said arterial connector are formed from a shape memory material.

12. The anastomotic of claim 1 wherein the venous connector and the arterial connector have a column pitch that is substantially equivalent along the length of a body of the venous and arterial connector.

13. The anastomotic of claim 1 wherein the outer diameter of the distal end of the arterial connector is from 3-5 mm.

14. The anastomotic connector of claim 1 wherein the inner diameter of the proximal end of the arterial connector is about 7 mm.

15. The anastomotic connector of claim 1 wherein a length of the arterial connector and the venous connector is from 4 cm to 8 cm.

16. The anastomotic connector of claim 1 wherein the outer diameter of the distal end of the venous connector is from 5 to 7 mm.

17. The anastomotic connector of claim 1 wherein said arterial connector includes an anchoring device that extends radially outwardly at an acute angle from a longitudinal axis of a tubular main body at the distal arterial end.

18. The anastomotic connector of claim 1 wherein the outer diameter of the proximal venous end is smaller than the inner diameter of the proximal arterial end.

19. The anastomotic connector of claim 1 wherein:
said arterial connector is configured to assume an outer diameter equal to an inner diameter of the arterial passageway when the arterial connector is deployed within the arterial passageway; and
said venous connector is configured to assume an outer diameter equal to an inner diameter of the venous passageway when the venous connector is deployed within the venous passageway.

* * * * *